(12) United States Patent
Qu et al.

(10) Patent No.: US 8,399,669 B2
(45) Date of Patent: Mar. 19, 2013

(54) TRI- AND TETRASUBSTITUTED PENTARYLENETETRACARBOXIMIDES

(75) Inventors: Jianqiang Qu, Ludwigshafen (DE); Neil Gregory Pschirer, Mainz (DE)

(73) Assignee: BASF SE, Ludwigshafen (DE)

( * ) Notice: Subject to any disclaimer, the term of this patent is extended or adjusted under 35 U.S.C. 154(b) by 229 days.

(21) Appl. No.: 12/989,293

(22) PCT Filed: Apr. 21, 2009

(86) PCT No.: PCT/EP2009/054751
§ 371 (c)(1),
(2), (4) Date: Oct. 22, 2010

(87) PCT Pub. No.: WO2009/130223
PCT Pub. Date: Oct. 29, 2009

(65) Prior Publication Data
US 2011/0039989 A1    Feb. 17, 2011

(30) Foreign Application Priority Data
Apr. 22, 2008 (EP) .................. 08154959

(51) Int. Cl.
*C07D 471/08* (2006.01)
*H01L 51/50* (2006.01)
*C09K 11/06* (2006.01)
(52) U.S. Cl. ............. 546/26; 313/504; 252/301.26
(58) Field of Classification Search ............ 546/26, 546/28; 313/504; 252/301.26
See application file for complete search history.

(56) References Cited

U.S. PATENT DOCUMENTS
8,202,994 B2 * 6/2012 Qu et al. ............. 546/41
2008/0188660 A1   8/2008 Pschirer et al.

FOREIGN PATENT DOCUMENTS
DE   10 2005 018 241   10/2006
WO        02 077081    10/2002
WO      2006 111511    10/2006

OTHER PUBLICATIONS

International Search Report issued Jun. 30, 2009 in PCT/EP09/054751 filed Apr. 21, 2009.
Pschirer, N.G. et al. "Pentarylene-and Hexary Lenebis (discarboximide)s: Near-Infrared-Absorbing Polyaromatic Dyes", Angewandte Chemie.International Edition, vol. 45, pp. 1401-1404, XP002474592 ( Jan. 1, 2006).
Quante, H. et al., "Quaterrylenebis (Discarboximides)", Angewandte Chemie. International Edition, vol. 34, No. 12, pp. 1323-1325, XP002002793 (Jul. 7, 1995).
U.S. Appl. No. 13/029,571, filed Feb. 17, 2011, Koenemann, et al.

* cited by examiner

Primary Examiner — Charanjit Aulakh

(74) *Attorney, Agent, or Firm* — Oblon, Spivak, McClelland, Maier & Neustadt, L.L.P.

(57) ABSTRACT

The present invention relates to pentarylenetetracarboximides of the formula (I) or (Ia) or mixtures thereof

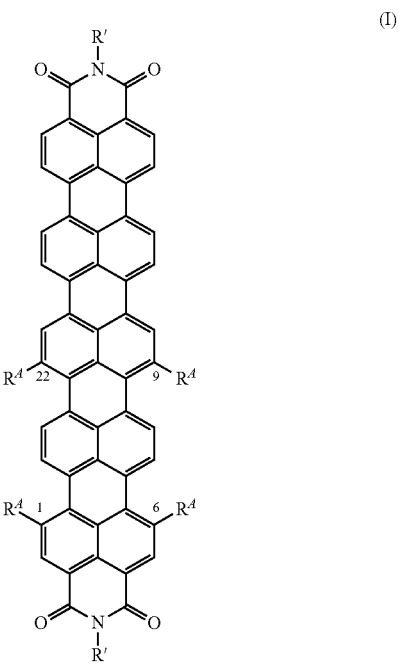

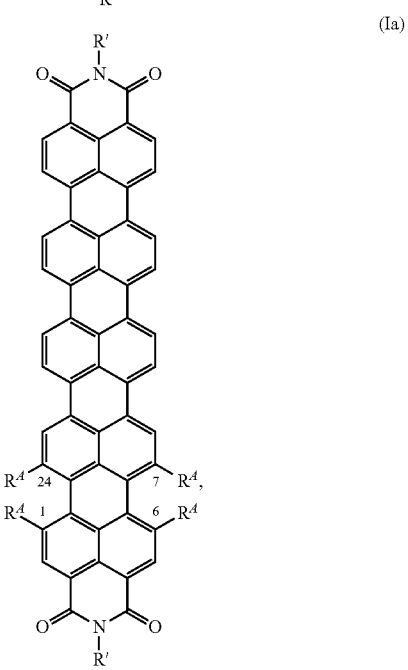

to processes for preparation thereof, and to the precursors and use thereof.

8 Claims, No Drawings

TRI- AND TETRASUBSTITUTED PENTARYLENETETRACARBOXIMIDES

The present invention relates to pentarylenetetracarboximides, to the preparation and precursors for preparation thereof, and to the use thereof.

Rylenetetracarboximides are known to be of particular interest from an application point of view owing to their strong absorption in the near infrared (NIR) region of the electromagnetic spectrum.

For example, WO-A 02/77081 describes the use of quaterrylenetetracarboximides as infrared absorbers for heat protection in glass laminates.

Pentarylene derivatives which are unsubstituted or have a low degree of substitution are described by N. G. Pschirer et al., Angew. Chem. Int. Ed. 45 (2006), 1401-1404.

Similar pentarylene derivatives are also described in DE-A 10 2005 018241.

In spite of the pentarylene derivatives already described and their use in connection with their absorption capacity in the NIR, there is a need for further, especially specifically substituted, derivatives, which in particular are simple to prepare.

It is thus an object of the present invention to provide such pentarylenetetracarboximides and processes for their preparation, which especially have advantages in the synthesis and good properties owing to their absorption capacity.

This object is achieved by a pentarylenetetracarboximide of the formula (I) or (Ia) or mixtures thereof

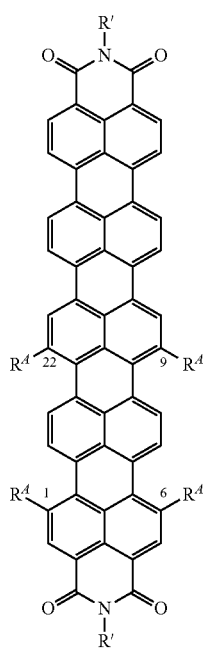

(I)

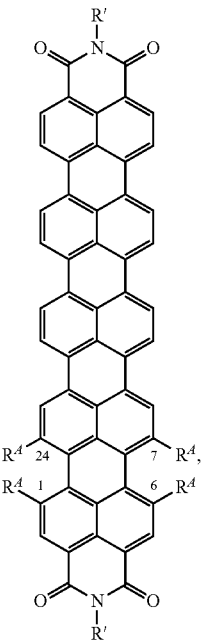

(Ia)

where
each $R^A$ is the same or different and is independently the following radical:
H;
aryloxy, arylthio, hetaryloxy or hetarylthio, to each of which may be fused further saturated or unsaturated 5- to 7-membered rings whose carbon skeleton may be interrupted by one or more —O—, —S—, —NR$^1$—, —N=CR$^1$—, —CO—, —SO— and/or —SO$_2$— moieties, where the entire ring system may be mono- or polysubstituted by the (i), (ii), (iii), (iv) and/or (v) radicals:

(i) $C_1$-$C_{30}$-alkyl whose carbon chain may be interrupted by one or more —O—, —S—, —NR$^1$—, —N=CR$^1$—, —C≡C—, —CR$^1$=CR$^1$—, —CO—, —SO— and/or —SO$_2$— moieties and which may be mono- or polysubstituted by: $C_1$-$C_{12}$-alkoxy, $C_1$-$C_6$-alkylthio, —C≡CR$^1$, —CR$^1$=CR$^1{}_2$, hydroxyl, mercapto, halogen, cyano, nitro, —NR$^2$R$^3$, —NR$^2$COR$^3$, —CONR$^2$R$^3$, —SO$_2$NR$^2$R$^3$, —COOR$^2$, —SO$_3$R$^2$, —PR$^2$R$^3$, —POR$^2$R$^3$, aryl and/or saturated or unsaturated $C_4$-$C_7$-cycloalkyl whose carbon skeleton may be interrupted by one or more —O—, —S—, —NR$^1$—, —N=CR$^1$—, —CR$^1$=CR$^1$—, —CO—, —SO— and/or —SO$_2$— moieties, where the aryl and cycloalkyl radicals may each be mono- or polysubstituted by $C_1$-$C_{18}$-alkyl and/or the above radicals specified as substituents for alkyl;

(ii) $C_3$-$C_8$-cycloalkyl whose carbon skeleton may be interrupted by one or more —O—, —S—, —NR$^1$—, —N=CR$^1$—, —CR$^1$=CR$^1$—, —CO—, —SO— and/or —SO$_2$— moieties and to which may be fused further saturated or unsaturated 5- to 7-membered rings whose carbon skeleton may be interrupted by one or more —O—, —S—, —NR$^1$—, —N=CR$^1$—, —CR$^1$=CR$^1$—, —CO—, —SO— and/or —SO$_2$— moieties, where the entire ring system may be mono- or polysubstituted by: $C_1$-$C_{18}$-alkyl, $C_1$-$C_{12}$-alkoxy, $C_1$-$C_6$-alkylthio, —C≡CR$^1$, —CR$^1$=CR$^1{}_2$, hydroxyl, mercapto, halogen, cyano, nitro, —NR$^2$R$^3$, —NR$^2$COR$^3$, —CONR$^2$R$^3$, —SO$_2$NR$^2$R$^3$, —COOR$^2$, —SO$_3$R$^2$, —PR$^2$R$^3$ and/or —POR$^2$R$^3$;

(iii) aryl or hetaryl to which may be fused further saturated or unsaturated 5- to 7-membered rings whose carbon skeleton may be interrupted by one or more —O—, —S—, —NR$^1$—, —N=CR$^1$—, —CR$^1$=CR$^1$—, —CO—, —SO— and/or —SO$_2$— moieties, where the entire ring system may be mono- or polysubstituted by: C$_1$-C$_{18}$-alkyl, C$_1$-C$_{12}$-alkoxy, C$_1$-C$_6$-alkylthio, —C≡CR$^1$, —CR$^1$=CR$^1{}_2$, hydroxyl, mercapto, halogen, cyano, nitro, —NR$^2$R$^3$, —NR$^2$COR$^3$, —CONR$^2$R$^3$, —SO$_2$NR$^2$R$^3$, —COOR$^2$, —SO$_3$R$^2$, —PR$^2$R$^3$, —POR$^2$R$^3$, aryl and/or hetaryl, each of which may be substituted by C$_1$-C$_{18}$-alkyl, C$_1$-C$_{12}$-alkoxy, hydroxyl, mercapto, halogen, cyano, nitro, —NR$^2$R$^3$, —NR$^2$COR$^3$, —CONR$^2$R$^3$, —SO$_2$NR$^2$R$^3$, —COOR$^2$, —SO$_3$R$^2$, —PR$^2$R$^3$ and/or —POR$^2$R$^3$;

(iv) a —U-aryl radical which may be mono- or polysubstituted by the above radicals specified as substituents for the aryl radicals (iii), where U is a —O—, —S—, —NR$^1$—, —CO—, —SO— or —SO$_2$— moiety;

(v) C$_1$-C$_{12}$-alkoxy, C$_1$-C$_6$-alkylthio, —C≡CR$^1$, —CR$^1$=CR$^1{}_2$, hydroxyl, mercapto, halogen, cyano, nitro, —NR$^2$R$^3$, —NR$^2$COR$^3$, —CONR$^2$R$^3$, —SO$_2$NR$^2$R$^3$, —COOR$^2$, —SO$_3$R$^2$, —PR$^2$R$^3$ and/or —POR$^2$R$^3$;

R$^1$ is hydrogen or C$_1$-C$_{18}$-alkyl, where the R$^1$ radicals may be the same or different when they occur more than once;

R$^2$, R$^3$ are each independently hydrogen;

C$_1$-C$_{18}$-alkyl whose carbon chain may be interrupted by one or more —O—, —S—, —CO—, —SO— and/or —SO$_2$— moieties and which may be mono- or polysubstituted by C$_1$-C$_{12}$-alkoxy, C$_1$-C$_6$-alkylthio, hydroxyl, mercapto, halogen, cyano, nitro and/or —COOR$^1$;

aryl or hetaryl, to each of which may be fused further saturated or unsaturated 5- to 7-membered rings whose carbon skeleton may be interrupted by one or more —O—, —S—, —CO— and/or —SO$_2$— moieties, where the entire ring system may be mono- or polysubstituted by C$_1$-C$_{12}$-alkyl and/or the above radicals specified as substituents for alkyl;

each R' is independently hydrogen;

C$_1$-C$_{30}$-alkyl whose carbon chain may be interrupted by one or more —O—, —S—, —NR$^1$—, —N=CR$^1$—, —CR$^1$=CR$^1$—, —CO—, —SO— and/or —SO$_2$— moieties and which may be mono- or polysubstituted by the (ii), (iii), (iv) and/or (v) radicals specified as substituents for the R$^A$ radicals;

C$_3$-C$_8$-cycloalkyl to which may be fused further saturated or unsaturated 5- to 7-membered rings whose carbon skeleton may be interrupted by one or more —O—, —S—, —N=CR$^1$—, —CR$^1$=CR$^1$—, —CO—, —SO— and/or —SO$_2$— moieties, where the entire ring system may be substituted by the (i), (ii), (iii), (iv) and/or (v) radicals specified as substituents for the R$^A$ radicals; or aryl or hetaryl to which may be fused further saturated or unsaturated 5- to 7-membered rings whose carbon skeleton may be interrupted by one or more —O—, —S—, —N=CR$^1$—, —CR$^1$=CR$^1$—, —CO—, —SO— and/or —SO$_2$— moieties, where the entire ring system may be substituted by the (i), (ii), (iii), (iv), (v) radicals specified as substituents for the R$^A$ radicals, aryl- and/or hetarylazo, each of which may be substituted by C$_1$-C$_{10}$-alkyl, C$_1$-C$_6$-alkoxy and/or cyano;

with the proviso that at least three R$^A$ in formula (I) or (Ia) are different than H.

This object is further achieved by a process for preparing the inventive pentarylenetetracarboximides, comprising the steps of (a) coupling at least one terrylene compound of the formula (II) or (IIa)

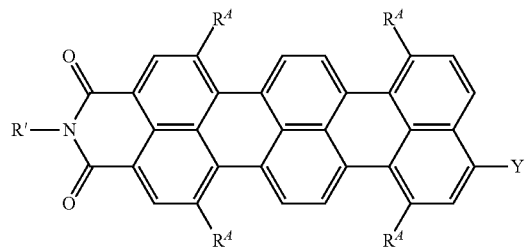

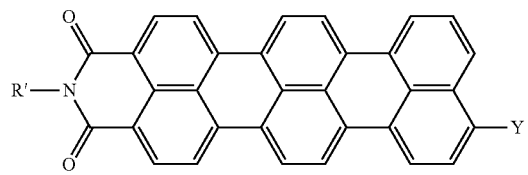

with at least one compound of the formula (III) or (IIIa)

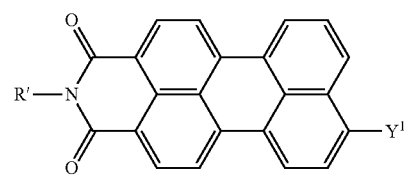

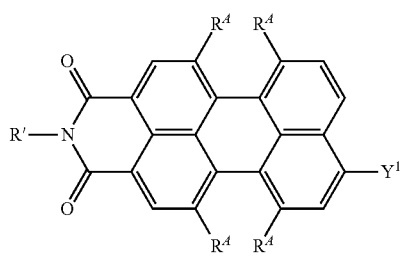

where

Y, Y$^1$ are each halogen or one radical of Y, Y$^1$ is halogen and the other is B(OR")$_2$;

each R" is independently hydrogen, C$_1$-C$_{30}$-alkyl, C$_5$-C$_8$-cycloalkyl, aryl or hetaryl or, joined together to form a 5- to 7-membered ring comprising the two oxygen atoms and the boron atom, may be fused to the unsaturated or saturated rings, where said ring may be substituted on the carbon atoms by up to 4 C$_1$-C$_{30}$-alkyl, C$_5$-C$_8$-cycloalkyl, aryl or hetaryl groups;

each R' and R$^A$ is as defined in claim 1;

(b) cyclodehydrogenating the reaction product obtained in step (a) to give a pentarylene compound of the general formula (I) or (Ia) or mixtures thereof.

This is because it has been found that, surprisingly, specific tetrasubstituted pentarylenetetracarboximides which have a substituent in the 1,6,9,22 or in the 1,6,7,24 positions, and also trisubstituted derivatives which are unsubstituted in one of these positions, could have obtained, the reactants selected in each case being two starting compounds, one starting compound having all substituents, and so the other being unsubstituted in relation to the $R^A$ substituents. These starting materials are very inexpensive starting materials, and a synthesis has surprisingly been found to be possible without solubility problems occurring as a result of the fact that one subunit is unsubstituted.

Preferred pentarylenetetracarboximides according to the present invention or mixtures thereof are those where all four $R^A$ substituents in formula (I) or (Ia) are different than H.

Alternatively, it is preferred that pentarylenetetracarboximides of the present invention or mixtures thereof are those in which $R^A$ in the 22 position in formula (I) or $R^A$ in the 24 position in formula (Ia) is H. At least some of these can be obtained by virtue of the fact that, in step (b) of the process according to the invention, proceeding from the tetra-substituted compounds, these lose an $R^A$ substituent, such that especially mixtures of tri- and tetrasubstituted pentarylenetetracarboximides may be present.

Preference is given to pentarylenetetracarboximides according to the present invention or mixtures thereof of the formula (I).

The reaction products obtained in step (a) of the process according to the invention for preparing the inventive pentarylenetetracarboximides serve as starting compounds in step (b) of the process according to the invention (cyclodehydrogenation).

The present invention therefore further provides pentarylenetetracarboximide precursors of the formula (Ib) or (Ic) or mixtures thereof

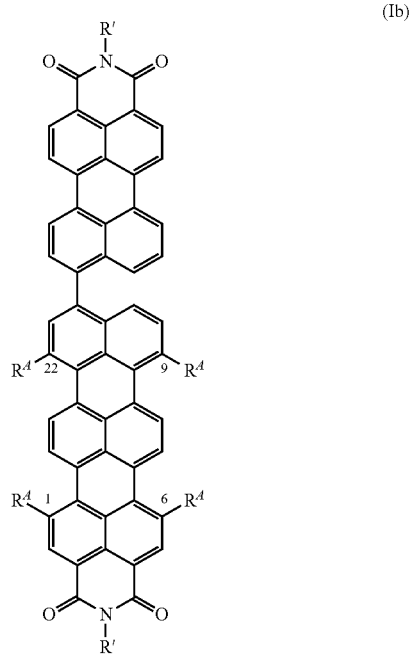

(Ib)

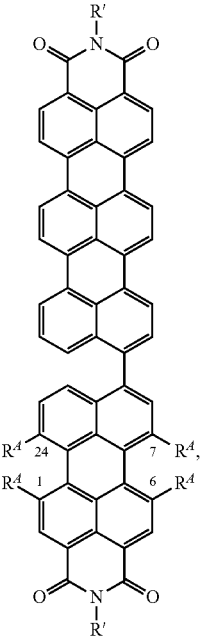

(Ic)

where each R' and $R^A$ is as defined in claim 1.

The inventive pentarylene compounds can thus be obtained with the aid of the process according to the invention by coupling an appropriate terrylene compound with the appropriate perylene compound. The inventive pentarylene compounds have three or four $R^A$ substituents which are present correspondingly in the positions specified in formulae (I) and (Ia).

The starting compounds of the formulae (II), (III), (IIIa) are known from the prior art or can be prepared with the aid of literature syntheses of analogous compounds. Especially terrylene derivatives which can serve as starting materials for the process according to the invention for preparing pentarylenetetracarboximides are described in DE-A 10 2005 018241. The inventive imide compounds can be prepared analogously.

The process according to the invention for preparing pentarylenetetracarboximides comprises, as the first step (a), the coupling of at least one terrylene compound of the formula (II) or (IIa) with a compound of the formula (III) or (IIIa), where the two units are linked in each case with the aid of the Y and $Y^1$ groups.

In this case, Y and $Y^1$ may be halides, through which the desired bonding of the two aromatic units is enabled with the aid of a catalytic coupling. It is equally possible that one of the Y, $Y^1$ radicals may be a halide and the other may be a boronic acid or a similar compound of the formula $B(OR")_2$. In that case, coupling is effected via what is known as the Suzuki reaction. In both cases, the halides are preferably bromide or chloride.

The inventive diimides are prepared with the aid of the process according to the invention preferably in the presence of an organic solvent, if desired in a mixture with water, and of a transition metal catalyst and of a base, and, as has been stated above, one of the two units may be a boronic acid derivative and the other a halide. Such a boronic acid derivative is obtainable, for example, by reacting the corresponding halogenated aromatic with the aid of diboranes of the general formula (IV) $(R"O)_2B—B(OR')_2$ in the presence of an aprotic organic solvent, of a transition metal catalyst and of a base.

Suitable diboranes of the general formula (IV) are especially bis(1,2- and 1,3-diolato)diboranes, tetraalkoxydiboranes, tetracycloalkoxydiboranes and tetra(het)aryloxydiboranes and their mixed forms. Examples of these compounds include: bis(pinacolato)diborane, bis(1,2-benzodiolato)diborane, bis(2,2-dimethyl-1,3-propanediolato)diborane, bis(1,1,3,3-tetramethyl-1,3-propanediolato)diborane, bis(4,5-pinanediolato)diborane, bis(tetramethoxy)diborane, bis(tetracyclopentoxy)diborane, bis(tetraphenoxy)diborane and bis(4-pyridiyloxy)diborane.

Preference is given to diboranes of the general formula (IV) in which the two R" radicals on a boron atom are joined together with formation of a five-membered or six-membered ring which comprises the two oxygen atoms and the boron atom. Aromatic or saturated, including bicyclic, rings having 5 to 7 carbon atoms as ring members may be fused to the five- or six-membered rings formed. All rings or ring systems may be substituted by up to 4 $C_1$-$C_{30}$-alkyl, $C_5$-$C_8$-cycloalkyl, aryl and/or hetaryl radicals; they are preferably substituted by up to 4 $C_1$-$C_4$-alkyl radicals. Examples of these preferred diboranes are the bis(1,2- and 1,3-diolato)diboranes already mentioned above, particular preference being given to bis(pinacolato)diborane.

The molar ratio of diborane of the general formula (IV) to the halogenated aromatic is generally 0.8:1 to 3:1, especially 1.5:1 to 2:1.

Suitable solvents are in principle all aprotic solvents which are stable toward bases under the reaction conditions and have a boiling point above the selected reaction temperature, in which the reactants dissolve completely at reaction temperature and the catalysts and bases used at least partially, so that substantially homogeneous reaction conditions are present. It is possible to use either nonpolar aprotic or polar aprotic solvents.

Examples of preferred nonpolar aprotic solvents are solvents which boil at >100° C. from the following groups: aliphatics (especially $C_8$-$C_{18}$-alkanes), unsubstituted, alkyl-substituted and fused cycloaliphatics (especially unsubstituted $C_7$-$C_{10}$-cycloalkanes, $C_6$-$C_8$-cycloalkanes which are substituted by one to three $C_1$-$C_6$-alkyl groups, polycyclic saturated hydrocarbons having 10 to 18 carbon atoms), alkyl- and cycloalkyl-substituted aromatics (especially benzene which is substituted by one to three $C_1$-$C_6$-alkyl groups or one $C_5$-$C_8$-cycloalkyl radical) and fused aromatics which may be alkyl-substituted and/or partly hydrogenated (especially naphthalene which is substituted by one to four $C_1$-$C_6$-alkyl groups) and mixtures of these solvents.

Examples of particularly preferred solvents include: octane, isooctane, nonane, isononane, decane, isodecane, undecane, dodecane, hexadecane and octadecan; cycloheptane, cyclooctane, methylcyclohexane, dimethylcyclohexane, trimethylcyclohexane, ethylcyclohexane, diethylcyclohexane, propylcyclohexane, isopropylcyclohexane, dipropylcyclohexane, butylcyclohexane, tert-butylcyclohexane, methylcycloheptane and methylcyclooctane; toluene, o-, m- and p-xylene, 1,3,5-trimethylbenzene (mesitylene), 1,2,4- and 1,2,3-trimethylbenzene, ethylbenzene, propylbenzene, isopropylbenzene, butylbenzene, isobutylbenzene, tert-butylbenzene and cyclohexylbenzene; naphthalene, decahydronaphthalene (decalin), 1- and 2-methylnaphthalene and 1- and 2-ethylnaphthalene; combinations of the aforementioned solvents, as can be obtained from the high-boiling, partly or fully hydrogenated fractions of thermal and catalytic cracking processes in crude oil or naphtha processing, for example mixtures of the Exxsol® type and alkylbenzene mixtures of the Solvesso® type.

Very particularly preferred solvents are xylene (all isomers), mesitylene and in particular toluene.

Examples of suitable polar-aprotic solvents are N,N-disubstituted aliphatic carboxamides (especially N,N-di-$C_1$-$C_4$-alkyl-$C_1$-$C_4$-carboxamides), nitrogen-containing heterocycles and aprotic ethers (especially cyclic ethers, diaryl ethers and di-$C_1$-$C_6$-alkyl ethers of monomeric and oligomeric $C_2$-$C_3$-alkylene glycols which may comprise up to 6 alkylene oxide units, in particular diethylene glycol di-$C_1$-$C_4$-alkyl ethers).

Examples of particularly suitable solvents include: N,N-dimethylformamide, N,N-diethylformamide, N,N-dimethylacetamide and N,N-dimethylbutyramide; N-methyl-2-pyrrolidone, quinoline, isoquinoline, quinaldine, pyrimidine, N-methylpiperidine and pyridine; tetrahydrofuran, dioxane, diphenyl ether, the dimethyl, diethyl, dipropyl, diisopropyl, di-n-butyl, di-sec-butyl and di-tert-butyl ethers of diethylene glycol, diethylene glycol methyl ethyl ether, triethylene glycol dimethyl ether, triethylene glycol diethyl ether and triethylene glycol methyl ethyl ether.

The amount of solvent is generally 10 to 1000 ml, preferably 20 to 300 ml, per g of halogenated aromatic.

Suitable transition metal catalysts are in particular palladium complexes, which are in turn generally used in amounts of 1 to 20 mol %, in particular 2 to 10 mol %, based on the halogenated aromatic.

Examples of such catalysts are tetrakis(triphenylphosphine)palladium(0), tetrakis(tris-o-tolylphosphine)palladium(0), [1,2-bis(diphenylphosphino)ethane]palladium(II) chloride, [1,1'-bis(diphenylphosphino)ferrocene]palladium(II) chloride, bis(triethylphosphine)palladium(II) chloride, bis(tricyclohexylphosphine)palladium(II) acetate, (2,2'-bipyridyl)palladium(II) chloride, bis(triphenylphosphine)palladium(II) chloride, tris(dibenzylideneacetone)dipalladium (0), 1,5-cyclooctadienepalladium(II) chloride, bis(acetonitrile)palladium(II) chloride and bis(benzonitrile)palladium(II) chloride, palladium(II) acetate, preference being given to [1,1'-bis(diphenylphosphino)ferrocene]palladium(II) chloride, tetrakis(triphenylphosphine)palladium(0) and palladium(II) acetate.

In general, the simultaneous presence of free ligand molecules is advisable, for example of tri(tert-butyl)phosphine, tri(i-butyl)phosphine, triphenylphosphine and tris(o-tolyl)phosphine, and 2-dicyclohexylphosphino-2,6-dimethoxybiphenyl. Typical amounts are 80 to 500 mol %, preferably 100 to 300 mol %, based on the transition metal catalyst.

Useful bases preferably include the alkali metal salts, especially the sodium salts and in particular the potassium salts, of weak organic and inorganic acids, such as sodium acetate, potassium acetate, sodium carbonate, sodium hydrogencarbonate, potassium carbonate and potassium hydrogencarbonate, phosphates, fluorides such as potassium fluoride. Preferred bases are the acetates, in particular potassium acetate.

Generally 1 to 5 mol, preferably 2 to 4 mol, of base are used per mole of halogenated aromatic.

The reaction temperature is typically 20 to 180° C., in particular 60 to 120° C.

The reaction time is generally 0.5 to 30 h, in particular 1 to 20 h.

In terms of process technology, the procedure in the preparation of the boronic acid derivatives is appropriately as follows:

The halogenated aromatic and solvent are initially charged, the diborane of the general formula (IV), the transition metal catalyst and the base are added successively and the mixture is heated to the desired reaction temperature under protective gas for 0.5 to 30 h. After cooling to room temperature, the solid constituents are filtered out of the reaction mixture and the solvent is distilled off under reduced pressure.

The Suzuki reaction of the boronic acid derivative thus prepared with the corresponding halogenated aromatic can in principle be used to prepare the product in step (a) of the process according to the invention under analogous conditions, in which case the corresponding boronic acid derivative instead of the diborane is reacted with the appropriate halogenated aromatic.

However, preference is given to reacting the boronic acid derivative with the halogenated aromatic in the presence of an organic solvent, if desired in a mixture with water, and of a transition metal catalyst and of a base performed, the molar ratio of boronic acid derivative to halogenated aromatic being generally 0.8:1 to 3:1, preferably 0.9:1 to 2:1.

Suitable solvents are all solvents in which the reactants dissolve completely at reaction temperature and the catalysts and bases used at least partially, so that substantially homogeneous reaction conditions are present.

Suitable examples are octane, isooctane, nonane, isononane, decane, isodecane, undecane, dodecane, hexadecane and octadecane; cycloheptane, cyclooctane, methylcyclohexane, dimethylcyclohexane, trimethylcyclohexane, ethylcyclohexane, diethylcyclohexane, propylcyclohexane, isopropylcyclohexane, dipropylcyclohexane, butylcyclohexane, tert-butylcyclohexane, methylcycloheptane and methylcyclooctane; toluene, o-, m- and p-xylene, 1,3,5-trimethylbenzene (mesitylene), 1,2,4- and 1,2,3-trimethylbenzene, ethylbenzene, propylbenzene, isopropylbenzene, butylbenzene, isobutylbenzene, tert-butylbenzene and cyclohexylbenzene; naphthalene, decahydronaphthalene (decalin), 1- and 2-methylnaphthalene and 1- and 2-ethylnaphthalene; combinations of the aforementioned solvents, as can be obtained from the high-boiling, partly or fully hydrogenated fractions of thermal and catalytic cracking processes in crude oil or naphtha processing, for example mixtures of the Exxsol® type and alkylbenzene mixtures of the Solvesso® type.

Very particularly preferred solvents are xylene (all isomers), mesitylene and in particular toluene.

The amount of solvent is typically 10 to 1000 ml, preferably 20 to 100 ml, per g of boronic acid derivative.

Preference is given to using water as an additional solvent. In this case, generally 10 to 1000 ml, in particular 250 to 500 ml, of water are used per l of organic solvent.

The transition metal catalysts used are likewise preferably palladium complexes. The amount of catalyst used is typically 1 to 20 mol %, in particular 1.5 to 5 mol %, based on the boronic acid derivative.

In general, the simultaneous presence of free ligand molecules is advisable, for example of tri(tert-butyl)phosphine, tri(i-butyl)phosphine, triphenylphosphine and tris(o-tolyl) phosphine and 2-dicyclohexylphosphino-2,6-dimethoxybiphenyl. Typical amounts are 80 to 500 mol %, preferably 100 to 300 mol %, based on the transition metal catalyst.

Preferred bases are alkali metal salts of weak acids, particular preference being given to the carbonates, such as sodium carbonate and in particular potassium carbonate. Preference is likewise also given here to phosphates, such as sodium phosphate or potassium phosphate. In general, the amount of bases is 0.1 to 10 mol, in particular 0.2 to 5 mol, per mole of boronic acid derivative.

The reaction temperature is generally 20 to 180° C., preferably 60 to 120° C. When water is used in step b), it is advisable not to undertake the reaction at temperatures above 100° C., since it is otherwise necessary to work under pressure.

The reaction has typically ended within 0.5 to 48 h, in particular within 5 to 20 h.

In terms of process technology, the procedure is appropriately as follows:

The boronic acid derivative and the halogenated aromatic and solvent are initially charged, transition metal catalyst and the base, preferably dissolved in water or a water/alcohol mixture, are added, and the mixture is heated to the desired reaction temperature under protective gas for 0.5 to 48 h. After cooling to room temperature, the organic phase is separated from the reaction mixture and the solvent is distilled off under reduced pressure.

The purity of the thus prepared product from step (a) of the process according to the invention for preparing the pentarylenetetracarboximides is generally sufficient for the further reaction in step (b). If appropriate, the crude product can be purified further by washing with water and, if desired, a suitable organic solvent, especially a chlorinated aliphatic or aromatic hydrocarbon, or by column chromatography on silica gel with a mixture of methylene chloride and hexane or pentane or with toluene as the eluent.

The yield in step a) of the process according to the invention is typically 20 to 95%.

In addition to the above-described Suzuki reaction, which requires a corresponding boronic acid derivative, a direct coupling, especially in the case of homo couplings, of halides can also be effected.

In this case, the reaction of the correspondingly halogenated aromatics of the formula (II) or (IIa) and (III) or (IIIa) can be effected in the presence of a diborane of the general formula (IV). Finally, a Suzuki reaction likewise proceeds, except that the corresponding boronic acid derivative is generated only in situ.

The coupling can be effected, for example, in the presence of 30 to 70 mol %, based on the halogenated aromatic, of a diborane of the general formula (IV), of a transition metal catalyst, of a base and of an aprotic solvent by a Suzuki coupling reaction, in which case the boronic acid derivative formed in situ is not intermediately isolated but rather reacted directly with the remaining halogenated aromatic.

In this process variant, the procedure is analogous to the above, except that, for example, only 30 to 70 mol % of diborane of the general formula (IV), based on the halogenated aromatic, is used.

Generally 1 to 20 mol %, preferably 5 to 10 mol %, of transition metal catalyst, and 1 to 5 mol, preferably 2 to 3 mol, of base are used per mole of halogenated aromatic. The aprotic organic solvent is used typically in amounts of 10 to 100 ml, in particular 20 to 50 ml, per g of halogenated aromatic.

The reaction temperature is generally 20 to 100° C., preferably 60 to 80° C., and the reaction time is 12 to 72 h, preferably 24 to 48 h.

In terms of process technology, the procedure is appropriately as follows:

The halogenated aromatic and solvent are initially charged, the diborane of the general formula (IV), the transition metal catalyst and the base are added in succession, and the mixture is heated to the desired reaction temperature for 12 to 72 h. After cooling to room temperature, the organic phase is removed from the reaction mixture and the solvent is distilled off under reduced pressure.

Here too, the purity of the resulting product is generally sufficient for the subsequent cyclodehydrogenation in step (b) of the process according to the invention. Further purification is possible, for example, by column chromatography.

The yield is typically 80 to 95%.

An additional possibility is to perform a direct coupling of the halogenated aromatics (halogen compound) without using a diborane.

This coupling can be effected, for example, in the presence of an organic transition metal complex as a catalyst, free ligand molecules and an aprotic solvent in a homo coupling.

Suitable inert diluents are, for example, aliphatic carboxamides such as N,N-dimethylformamide and N,N-dimethylacetamide, aliphatic and cycloaliphatic ethers such as 1,2-dimethoxyethane, and aromatics such as benzene, toluene and xylene, preference being given to N,N-dimethylformamide and N,N-dimethylacetamide.

The amount of diluent is generally 20 to 100 g, preferably 25 to 45 g, per gram of halogen compound.

Useful organic transition metal complexes which serve as the catalyst include, as well as the known palladium complexes such as tetrakis(triphenylphosphine)palladium(0), especially nickel complexes, for example bis(triphenylphosphine)nickel(II) chloride, tetrakis(triphenylphosphine)nickel (0), [1,2-bis(diphenylphosphino)ethane]nickel(II) chloride and preferably bis(1,5-cyclooctadiene)nickel(0). The catalysts can also be obtained by the addition of transition metal salts or compounds, free ligands such as cyclooctadiene, bipyridyl, triphenylphosphine, trifluorophosphine, η-, δ- and π-bonded olefins, cycloolefins, aromatics and antiaromatics, carbonyls, hydrogen and halogen, and also mixtures thereof, and, if required, oxidizing and reducing agents.

Generally 40 to 150 mol %, preferably 50 to 100 mol %, of organic transition metal complex based on the halogen compound used is used.

In general, the simultaneous presence of free ligand molecules is always advisable, especially mixtures of cyclooctadiene and bipyridyl in a molar ratio of 1:1 to 8:1. Suitable amounts here are typically 80 to 900 mol %, preferably 80 to 200 mol %, preferably based on the halogen compound.

The coupling temperature is generally 40 to 80° C., preferably 60 to 70° C.

The reaction time is generally 24 to 48 h, in particular 36 to 48 h.

In terms of process technology, the procedure in this direct coupling is appropriately to initially charge the halogen compound, the organometallic catalyst and free ligand molecules in the inert diluent and, if appropriate under protective gas, to heat to the desired reaction temperature for 24 to 48 h. After cooling, the reaction mixture is introduced into water which may comprise methanol if appropriate, dilute inorganic acid, for example dilute hydrochloric acid, is added and the precipitate formed is filtered off, washed with water and dried under reduced pressure.

The purity of the inventive product thus produced is generally sufficient for the subsequent cyclodehydrogenation in step (b) of the process according to the invention. If appropriate, the product may additionally be purified further by column chromatography on silica gel with a mixture of methylene chloride and hexane or pentane as the eluent.

The yield is generally 20 to 60%.

In step (b) of the process according to the invention, the cyclodehydrogenation of the reaction product obtained in step (a) takes place. The cyclodehydrogenation can be undertaken in an organic reaction medium which has hydroxyl and amino functions and comprises an essentially undissolved base or in the presence of a base-stable high-boiling organic solvent and of an alkali metal or alkaline earth metal base and a nitrogen-containing auxiliary base.

Preference is given to the former process variant. Suitable organic reaction media here are in particular amino alcohols which have 2 to 20, preferably 2 to 10, carbon atoms. The carbon chain of these alcohols can be interrupted by oxygen atoms in ether function. Examples of particularly suitable solvents are ethanolamine, triethanolamine and diethanolamine, preference being given to ethanolamine. It is also possible to use mixtures of alcohols and amines which each have a boiling point of at least 70° C. and are liquid at the reaction temperature. It is also possible to use corresponding glycols, mono- and dialkyl glycol ethers as an alternative or in a mixture to the above-mentioned media. In this context, it is possible to use mono-, di-, tri-, oligo- or polyalkylene glycols or glycol ethers. Examples are ethylene glycol, ethylene glycol monoethyl ether, ethylene glycol diethyl ether, diethylene glycol monoethyl ether or diethylene glycol diethyl ether.

Typically 1.5 to 150 ml, preferably 5 to 50 ml, of reaction medium are used per gram of starting compound.

Suitable bases essentially insoluble in the reaction medium are the alkali metal salts, especially the sodium salts and in particular the potassium salts, of weak organic and preferably weak inorganic acids, such as formates, acetates, propionates, hydrogen-carbonates and more preferably carbonates, especially sodium carbonate and in particular potassium carbonate.

In general, the amount of base is 1 to 10 mol, preferably 2 to 5 mol, per mole of starting compound.

The reaction temperature is generally 40 to 200° C., in particular 80 to 160° C.

The reaction time is typically 0.5 to 64 h, preferably 1 to 12 h.

In terms of process technology, the procedure is appropriately to stir a mixture of starting compound, solvent and base at the desired reaction temperature under protective gas for 0.5 to 24 h, and to precipitate the inventive product of the formula (I) or (Ia) formed, after cooling to room temperature, out of the reaction mixture by adding an alcohol, such as ethanol, or water, to filter it off and to wash it with water.

The inventive rylene compound can be purified by removing catalyst residues by a rapid filtration through silica gel while washing it with a halogenated aliphatic hydrocarbon such as methylene chloride. Residues of unconverted reactants can be removed by column chromatography on silica gel with methylene chloride as the eluent or by repeated washing with hexane or pentane.

The yield is generally 50 to 100%.

The product obtained by the process according to the invention for preparing pentarylenetetracarboximides is diimides of the general formula (I) or (Ia)

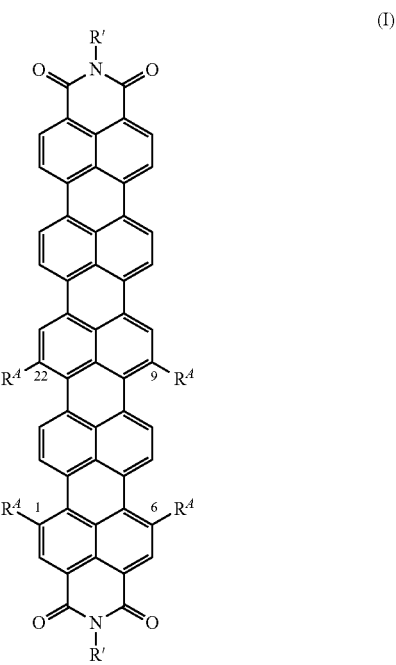

(I)

-continued

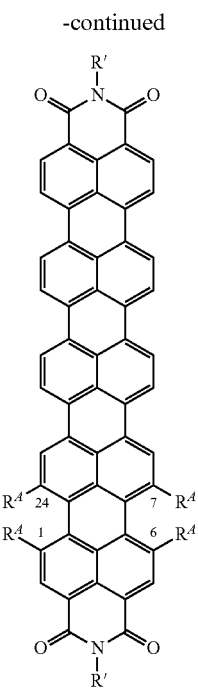

(Ia)

or mixtures thereof. In these structures, the variables $R^4$, R' are each as defined above.

Specific examples of the $R^4$, R', R", $R^1$ to $R^3$ radicals mentioned in the formulae and their substituents include:

Examples of alkyls are methyl, ethyl, propyl, isopropyl, butyl, isobutyl, tert-butyl, pentyl, isopentyl, neopentyl, tert-pentyl, hexyl, 2-methylpentyl, heptyl, 1-ethylpentyl, octyl, 2-ethylhexyl, isooctyl, nonyl, isononyl, decyl, isodecyl, undecyl, dodecyl, tridecyl, isotridecyl, tetradecyl, pentadecyl, hexadecyl, heptadecyl, octadecyl, nonadecyl and eicosyl (the above terms isooctyl, isononyl, isodecyl and isotridecyl are trivial terms and stem from the alcohols obtained by the oxo process). The numbers specified as indices after the symbol "C" refer to the maximum and minimum number of carbon atoms in the alkyls.

Examples of alkyls interrupted by oxygen are 2-methoxyethyl, 2-ethoxyethyl, 2-propoxyethyl, 2-isopropoxyethyl, 2-butoxyethyl, 2- and 3-methoxypropyl, 2- and 3-ethoxypropyl, 2- and 3-propoxypropyl, 2- and 3-butoxypropyl, 2- and 4-methoxybutyl, 2- and 4-ethoxybutyl, 2- and 4-propoxybutyl, 3,6-dioxaheptyl, 3,6-dioxaoctyl, 4,8-dioxanonyl, 3,7-dioxaoctyl, 3,7-dioxanonyl, 4,7-dioxaoctyl, 4,7-dioxanonyl, 2- and 4-butoxybutyl, 4,8-dioxadecyl, 3,6,9-trioxadecyl, 3,6,9-trioxaundecyl, 3,6,9-trioxadodecyl, 3,6,9,12-tetraoxamidecyl and 3,6,9,12-tetraoxatetradecyl.

Examples of alkyls interrupted by sulfur are 2-methylthioethyl, 2-ethylthioethyl, 2-propylthioethyl, 2-isopropylthioethyl, 2-butylthioethyl, 2- and 3-methylthiopropyl, 2- and 3-ethylthiopropyl, 2- and 3-propylthiopropyl, 2- and 3-butylthiopropyl, 2- and 4-methylthiobutyl, 2- and 4-ethylthiobutyl, 2- and 4-propylthiobutyl, 3,6-dithiaheptyl, 3,6-dithiaoctyl, 4,8-dithianonyl, 3,7-dithiaoctyl, 3,7-dithianonyl, 2- and 4-butylthiobutyl, 4,8-dithiadecyl, 3,6,9-trithiadecyl, 3,6,9-trithiaundecyl, 3,6,9-trithiadodecyl, 3,6,9,12-tetrathiamidecyl and 3,6,9,12-tetrathiatetradecyl.

Examples of alkyls interrupted by amino groups are 2-monomethyl- and 2-monoethylaminoethyl, 2-dimethylaminoethyl, 2- and 3-dimethylaminopropyl, 3-monoisopropylaminopropyl, 2- and 4-monopropylaminobutyl, 2- and 4-dimethylaminobutyl, 6-methyl-3,6-diazaheptyl, 3,6-dimethyl-3,6-diazaheptyl, 3,6-diazaoctyl, 3,6-dimethyl-3,6-diazaoctyl, 9-methyl-3,6,9-triazadecyl, 3,6,9-trimethyl-3,6,9-triazadecyl, 3,6,9-triazaundecyl, 3,6,9-trimethyl-3,6,9-triazaundecyl, 12-methyl-3,6,9,12-tetraazamidecyl and 3,6,9,12-tetramethyl-3,6,9,12-tetraazamidecyl.

Further examples of alkyl groups which are interrupted and/or have substituents are:
(1-ethylethylidene)aminoethylene, (1-ethylethylidene)aminopropylene, (1-ethylethylidene)aminobutylene, (1-ethylethylidene)aminodecylene and (1-ethylethylidene)aminododecylene;
propan-2-on-1-yl, butan-3-on-1-yl, butan-3-on-2-yl and 2-ethylpentan-3-on-1-yl;
2-methylsulfoxidoethyl, 2-ethylsulfoxidoethyl, 2-propylsulfoxidoethyl, 2-isopropylsulfoxidoethyl, 2-butylsulfoxidoethyl, 2- and 3-methylsulfoxidopropyl, 2- and 3-ethylsulfoxidopropyl, 2- and 3-propylsulfoxidopropyl, 2- and 3-butylsulfoxidopropyl, 2- and 4-methylsulfoxidobutyl, 2- and 4-ethylsulfoxidobutyl, 2- and 4-propylsulfoxidobutyl and 4-butylsulfoxidobutyl;
2-methylsulfonylethyl, 2-ethylsulfonylethyl, 2-propylsulfonylethyl, 2-isopropylsulfonylethyl, 2-butylsulfonylethyl, 2- and 3-methylsulfonylpropyl, 2- and 3-ethylsulfonylpropyl, 2- and 3-propylsulfonylpropyl, 2- and 3-butylsulfonylpropyl, 2- and 4-methylsulfonylbutyl, 2- and 4-ethylsulfonylbutyl, 2- and 4-propylsulfonylbutyl and 4-butylsulfonylbutyl; carboxymethyl, 2-carboxyethyl, 3-carboxypropyl, 4-carboxybutyl, 5-carboxypentyl, 6-carboxyhexyl, 8-carboxyoctyl, 10-carboxydecyl, 12-carboxydodecyl and 14-carboxytetradecyl;
sulfomethyl, 2-sulfoethyl, 3-sulfopropyl, 4-sulfobutyl, 5-sulfopentyl, 6-sulfohexyl, 8-sulfooctyl, 10-sulfodecyl, 12-sulfododecyl and 14-sulfotetradecyl;
2-hydroxyethyl, 2- and 3-hydroxypropyl, 1-hydroxyprop-2-yl, 3- and 4-hydroxybutyl, 1-hydroxybut-2-yl and 8-hydroxy-4-oxaoctyl;
2-cyanoethyl, 3-cyanopropyl, 3- and 4-cyanobutyl, 2-methyl-3-ethyl-3-cyanopropyl, 7-cyano-7-ethylheptyl and 4,7-dimethyl-7-cyanoheptyl;
2-chloroethyl, 2- and 3-chloropropyl, 2-, 3- and 4-chlorobutyl, 2-bromoethyl, 2- and 3-bromopropyl and 2-, 3- and 4-bromobutyl;
2-nitroethyl, 2- and 3-nitropropyl and 2-, 3- and 4-nitrobutyl.

Examples of alkyloxy are methoxy, ethoxy, propoxy, isopropoxy, butoxy, isobutoxy, sec-butoxy, tert-butoxy, pentoxy, isopentoxy, neopentoxy, tert-pentoxy and hexoxy.

Examples of alkylthio are methylthio, ethylthio, propylthio, isopropylthio, butylthio, isobutylthio, sec-butylthio, tert-butylthio, pentylthio, isopentylthio, neopentylthio, tert-pentylthio and hexylthio.

Examples of radicals with a triple bond are ethynyl, 1- and 2-propynyl, 1-, 2- and 3-butynyl, 1-, 2-, 3- and 4-pentynyl, 1-, 2-, 3-, 4- and 5-hexynyl, 1-, 2-, 3-, 4-, 5-, 6-, 7-, 8- and 9-decynyl, 1-, 2-, 3-, 4-, 5-, 6-, 7-, 8-, 9-, 10- and 11-dodecynyl and 1-, 2-, 3-, 4-, 5-, 6-, 7-, 8-, 9-, 10-, 11-, 12-, 13-, 14-, 15-, 16- and 17-octadecynyl.

Examples of radicals with a double bond are ethenyl, 1- and 2-propenyl, 1-, 2- and 3-butenyl, 1-, 2-, 3- and 4-pentenyl, 1-, 2-, 3-, 4- and 5-hexenyl, 1-, 2-, 3-, 4-, 5-, 6-, 7-, 8- and 9-decenyl, 1-, 2-, 3-, 4-, 5-, 6-, 7-, 8-, 9-, 10- and 11-dodecenyl and 1-, 2-, 3-, 4-, 5-, 6-, 7-, 8-, 9-, 10-, 11-, 12-, 13-, 14-, 15-, 16- and 17-octadecenyl.

Examples of further radicals are
methylamino, ethylamino, propylamino, isopropylamino, butylamino, isobutylamino, pentylamino, hexylamino, dimethylamino, methylethylamino, diethylamino, dipropylamino, diisopropylamino, dibutylamino, diisobutylamino, dipentylamino, dihexylamino, dicyclopentylamino, dicyclohexylamino, dicycloheptylamino, diphenylamino and dibenzylamino;

formylamino, acetylamino, propionylamino and benzoylamino;

carbamoyl, methylaminocarbonyl, ethylaminocarbonyl, propylaminocarbonyl, butylaminocarbonyl, pentylaminocarbonyl, hexylaminocarbonyl, heptylaminocarbonyl, octylaminocarbonyl, nonylaminocarbonyl, decylaminocarbonyl and phenylaminocarbonyl;

aminosulfonyl, N,N-dimethylaminosulfonyl, N,N-diethylaminosulfonyl, N-methyl-N-ethylaminosulfonyl, N-methyl-N-dodecylaminosulfonyl, N-dodecylaminosulfonyl, (N,N-dimethylamino)ethylaminosulfonyl, N,N-(propoxyethyl)dodecylaminosulfonyl, N,N-diphenylaminosulfonyl, N,N-(4-tert-butylphenyl)octadecylaminosulfonyl and N,N-bis(4-chlorophenyl)aminosulfonyl;

methoxycarbonyl, ethoxycarbonyl, propoxycarbonyl, isopropoxycarbonyl, hexoxycarbonyl, dodecyloxycarbonyl, octadecyloxycarbonyl, phenoxycarbonyl, (4-tert-butylphenoxy)carbonyl and (4-chlorophenoxy)carbonyl;

methoxysulfonyl, ethoxysulfonyl, propoxysulfonyl, isopropoxysulfonyl, butoxysulfonyl, isobutoxysulfonyl, tert-butoxysulfonyl, hexoxysulfonyl, dodecyloxysulfonyl, octadecyloxysulfonyl, phenoxysulfonyl, 1- and 2-naphthyloxysulfonyl, (4-tert-butylphenoxy)sulfonyl and (4-chlorophenoxy)sulfonyl;

diphenylphosphino, di-(o-tolyl)phosphino and diphenylphosphinoxido.

Halogens are chlorine, bromine and iodine.

Aryl- or hetarylazo are, for example, phenylazo, 2-naphthylazo, 2-pyridylazo and 2-pyrimidylazo.

Optionally substituted cycloalkyls are, for example, cyclopropyl, cyclobutyl, cyclopentyl, 2- and 3-methylcyclopentyl, 2- and 3-ethylcyclopentyl, cyclohexyl, 2-, 3- and 4-methylcyclohexyl, 2-, 3- and 4-ethylcyclohexyl, 3- and 4-propylcyclohexyl, 3- and 4-isopropylcyclohexyl, 3- and 4-butylcyclohexyl, 3- and 4-sec-butylcyclohexyl, 3- and 4-tert-butylcyclohexyl, cycloheptyl, 2-, 3- and 4-methylcycloheptyl, 2-, 3- and 4-ethylcycloheptyl, 3- and 4-propylcycloheptyl, 3- and 4-isopropylcycloheptyl, 3- and 4-butylcycloheptyl, 3- and 4-sec-butylcycloheptyl, 3- and 4-tert-butylcycloheptyl, cyclooctyl, 2-, 3-, 4- and 5-methylcyclooctyl, 2-, 3-, 4- and 5-ethylcyclooctyl and 3-, 4- and 5-propylcyclooctyl; 3- and 4-hydroxycyclohexyl, 3- and 4-nitrocyclohexyl and 3- and 4-chlorocyclohexyl. The numbers specified as indices after the symbol "C" refer to the minimum and maximum number of carbon atoms in the cycloalkyls.

Examples of optionally interrupted cycloalkyls are
1-, 2- and 3-cyclopentenyl, 1-, 2-, 3- and 4-cyclohexenyl, 1-, 2- and 3-cycloheptenyl and 1-, 2-, 3- and 4-cyclooctenyl;
2-dioxanyl, 1-morpholinyl, 1-thiomorpholinyl, 2- and 3-tetrahydrofuryl, 1-, 2- and 3-pyrrolidinyl, 1-piperazyl, 1-diketopiperazyl and 1-, 2-, 3- and 4-piperidyl.

Optionally fused and/or substituted and/or interrupted aryl and hetaryl groups should have at least 3 to 14 ring atoms, preferably 5 to 10 ring atoms, and are, for example, phenyl, 2-naphthyl, 2- and 3-pyrryl, 2-, 3- and 4-pyridyl, 2-, 4- and 5-pyrimidyl, 3-, 4- and 5-pyrazolyl, 2-, 4- and 5-imidazolyl, 2-, 4- and 5-thiazolyl, 3-(1,2,4-triazyl), 2-(1,3,5-triazyl), 6-quinaldyl, 3-, 5-, 6- and 8-quinolinyl, 2-benzoxazolyl, 2-benzothiazolyl, 5-benzothiadiazolyl, 2- and 5-benzimidazolyl and 1- and 5-isoquinolyl;

1-, 2-, 3-, 4-, 5-, 6- and 7-indolyl, 1-, 2-, 3-, 4-, 5-, 6- and 7-isoindolyl, 5-(4-methylisoindolyl), 5-(4-phenylisoindolyl), 1-, 2-, 4-, 6-, 7- and 8-(1,2,3,4-tetrahydroisoquinolinyl), 3-(5-phenyl)-(1,2,3,4-tetrahydroisoquinolinyl), 5-(3-dodecyl-(1,2,3,4-tetrahydroisoquinolinyl), 1-, 2-, 3-, 4-, 5-, 6-, 7- and 8-(1,2,3,4-tetrahydroquinolinyl) and 2-, 3-, 4-, 5-, 6-, 7- and 8-chromanyl, 2-, 4- and 7-quinolinyl, 2-(4-phenylquinolinyl) and 2-(5-ethylquinolinyl);

2-, 3- and 4-methylphenyl, 2,4-, 3,5- and 2,6-dimethylphenyl, 2,4,6-trimethylphenyl, 2-, 3- and 4-ethylphenyl, 2,4-, 3,5- and 2,6-diethylphenyl, 2,4,6-triethylphenyl, 2-, 3- and 4-propylphenyl, 2,4-, 3,5- and 2,6-dipropylphenyl, 2,4,6-tripropylphenyl, 2-, 3- and 4-isopropylphenyl, 2,4-, 3,5- and 2,6-diisopropylphenyl, 2,4,6-triisopropylphenyl, 2-, 3- and 4-butylphenyl, 2,4-, 3,5- and 2,6-dibutylphenyl, 2,4,6-tributylphenyl, 2-, 3- and 4-isobutylphenyl, 2,4-, 3,5- and 2,6-diisobutylphenyl, 2,4,6-triisobutylphenyl, 2-, 3- and 4-sec-butylphenyl, 2,4-, 3,5- and 2,6-di-sec-butylphenyl and 2,4,6-tri-sec-butylphenyl; 2-, 3- and 4-methoxyphenyl, 2,4-, 3,5- and 2,6-dimethoxyphenyl, 2,4,6-trimethoxyphenyl, 2-, 3- and 4-ethoxyphenyl, 2,4-, 3,5- and 2,6-diethoxyphenyl, 2,4,6-triethoxyphenyl, 2-, 3- and 4-propoxyphenyl, 2,4-, 3,5- and 2,6-dipropoxyphenyl, 2-, 3- and 4-isopropoxyphenyl, 2,4- and 2,6-diisopropoxyphenyl and 2-, 3- and 4-butoxyphenyl; 2-, 3- and 4-chlorophenyl and 2,4-, 3,5- and 2,6-dichlorophenyl; 2-, 3- and 4-hydroxyphenyl and 2,4-, 3,5- and 2,6-dihydroxyphenyl; 2-, 3- and 4-cyanophenyl; 3- and 4-carboxyphenyl; 3- and 4-carboxamidophenyl, 3- and 4-N-methylcarboxamidophenyl and 3- and 4-N-ethylcarboxamidophenyl; 3- and 4-acetylaminophenyl, 3- and 4-propionylaminophenyl and 3- and 4-butyrylaminophenyl; 3- and 4-N-phenylaminophenyl, 3- and 4-N-(o-tolyl)aminophenyl, 3- and 4-N-(m-tolyl)aminophenyl and 3- and 4-N-(p-tolyl)aminophenyl; 3- and 4-(2-pyridyl)aminophenyl, 3- and 4-(3-pyridyl)aminophenyl, 3- and 4-(4-pyridyl)aminophenyl, 3- and 4-(2-pyrimidyl)aminophenyl and 4-(4-pyrimidyl)aminophenyl;

4-phenylazophenyl, 4-(1-naphthylazo)phenyl, 4-(2-naphthylazo)phenyl, 4-(4-naphthylazo)phenyl, 4-(2-pyridylazo)phenyl, 4-(3-pyridylazo)phenyl, 4-(4-pyridylazo)phenyl, 4-(2-pyrimidylazo)phenyl, 4-(4-pyrimidylazo)phenyl and 4-(5-pyrimidylazo)phenyl;

phenoxy, phenylthio, 2-naphthoxy, 2-naphthylthio, 2-, 3- and 4-pyridyloxy, 2-, 3- and 4-pyridylthio, 2-, 4- and 5-pyrimidyloxy and 2-, 4- and 5-pyrimidylthio.

The inventive diimides of the general formulae (I) and (Ia) or mixtures thereof are preferably those in which all $R^A$ are the same.

The inventive diimides of the general formulae (I) and (Ia) or mixtures thereof are likewise preferably those in which each $R^A$ is independently aryloxy or arylthio, where the entire ring system may be mono- or polysubstituted by the (i), (ii), (iii), (iv) and/or (v) radicals as specified above. It is especially preferred when $R^A$ may each independently be mono- or polysubstituted by a (i) radical.

The inventive diimides of the general formulae (I) and (Ia) or mixtures thereof are likewise preferably those in which each $R^A$ is independently

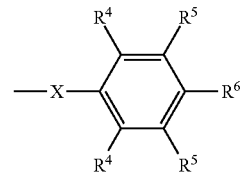

where

X is O or S and

R⁴, R⁵, R⁶ may each independently be hydrogen or the (i), (ii), (iii), (iv) and/or (v) radicals as specified above, with the proviso that at least one of the R⁴, R⁶ radicals is not hydrogen. It is especially preferred that when R⁴ is $C_1$-$C_{30}$-alkyl or $C_3$-$C_8$-cycloalkyl, a ternary carbon atom does not occur in the 1-position.

It is also preferred that neither R⁴ is hydrogen and R⁵, R⁶ are each hydrogen, or R⁶ is not hydrogen and R⁴, R⁵ are each hydrogen.

The inventive diimides of the general formulae (I) and (Ia) or mixtures thereof are likewise preferably those in which each R' is independently $C_1$-$C_{30}$-alkyl or aryl, where the entire ring system may be mono- or polysubstituted by the (i), (ii), (iii), (iv) and/or (v) radicals as specified above. Especially preferably, R' is mono- or polysubstituted by a (i) radical. Likewise preferably, all R' are identical.

The inventive diimides of the general formulae (I) and (Ia) exhibit strong absorption in the infrared region at wavelengths of 700 to 1100 nm.

They are therefore suitable, just like their precursors (Ib) and (Ic), for a multitude of uses, such as coloring high molecular weight organic and inorganic materials, for example coatings, printing inks and plastics, for producing aqueous polymer dispersions which absorb in the near infrared region of the electromagnetic spectrum, for obtaining markings and inscriptions which absorb infrared light and are invisible to the human eye, as infrared absorbers for heat management, as IR laser beam absorbing materials in the fusion treatment of plastics parts, as semiconductors in organic electronics, as emitters in electro- and chemiluminescence applications, or as active components in photovoltaics.

The present invention therefore further provides for the use of an inventive pentarylenetetracarboximide or precursor thereof or mixtures thereof for coloring high molecular weight organic and inorganic materials, as dispersing aids and pigment additives for organic pigments, for producing aqueous polymer dispersions which absorb in the near infrared region of the electromagnetic spectrum, for obtaining markings and inscriptions which absorb infrared light and are invisible to the human eye, as infrared absorbers for heat management, as IR laser beam absorbent materials in the fusion treatment of plastics parts, as semiconductors in organic electronics, as emitters in electro- and chemiluminescence applications or as active components in photovoltaics.

EXAMPLES

Example 1

Preparation of N-(2,6-diisopropylphenyl-1,6,9,14-tetra[2,6-diisopropylphenoxy]-11-(4,4,5,5-tetramethyl-1,3,2-dioxaboran-2-yl)terrylene-3,4-dicarboximide To a solution of 0.72 g (0.52 mmol) of N-(2,6-diisopropylphenyl-1,6,9,14-tetra-[2,6-diisopropylphenoxy]-11-bromoterrylene-3,4-dicarboximide in 25 ml of anhydrous toluene in a 50 ml Schlenk tube are added successively 0.33 g (1.3 mmol) of bis(pinacolato)diborane, 0.2 g (2.0 mmol) of sodium acetate and 0.2 g (0.26 mmol) of [1,1'-bis(diphenylphosphino)ferrocene]palladium(II) chloride. The resulting mixture is then heated to 70° C. under argon and kept at this temperature overnight. After cooling to room temperature, the product is extracted with methylene chloride and washed with water. The solvent is then distilled off. The solid residue is subjected to a column filtration on silica gel with 1:20 ethyl acetate/hexane as the eluent.

0.63 g of product is obtained in the form of a blue solid, which corresponds to a yield of 84%.

Analytical Data:

¹H NMR (500 MHz, CD₂Cl₂, 25° C.): δ=9.79 (m, 2H), 9.60 (m, 2H), 8.62 (d, 1H), 7.71 (s, 2H), 7.39 (t, 1H), 7.40-7.30 (m, 13H), 7.28 (d, 2H), 6.28 (d, 1H), 3.15 (m, 8H), 2.68 (m, 2H), 1.36 (s, 12H), 1.26 (d, 24H), 1.09 (d, 24H), 1.0 (d, 12H) ppm;

UV-Vis (CHCl₃): $\lambda_{max}$=672 nm;

MS (Maldi): m/z (rel. int.)=1435.7 (100%) [M+].

Example 2

Preparation of N-(2,6-diisopropylphenyl-1,6,9,14-tetra[2,6-diisopropylphenoxy]-11-(9-[N-(2,6-diisopropylphenyl)]perylene-3,4-dicarboximide)terrylene-3,4-dicarboximide To a mixture, stirred under N₂, of 0.143 g (0.1 mmol) of N-(2,6-diisopropylphenyl-1,6,9,14-tetra[2,6-diisopropylphenoxy]-11-(4,4,5,5-tetramethyl-1,3,2-dioxaboran-2-yl)terrylene-3,4-dicarboximide and 0.084 g (0.15 mmol) of N-(2,6-diisopropylphenyl-9-bromoperylene-3,4-dicarboximide in 15 ml of toluene are added first a solution of 0.038 g (0.28 mmol) of potassium carbonate in 4 ml of water and 0.4 ml of ethanol, and then 0.001 g (0.004 mmol) of palladium(II) acetate and 0.008 g (0.003 mmol) of 2-dicyclohexylphosphino-2,6-dimethoxybiphenyl. The mixture is heated to 90° C. under N₂ and stirred at this temperature for 14 h. After cooling to room temperature, the organic phase is removed and the solvent is drawn off under reduced pressure. The crude product is subjected to column chromatography on silica gel with toluene as the eluent.

116 mg of product are obtained in the form of a black-green solid, which corresponds to a yield of 65%.

Analytical Data:

MS (Maldi): m/z (rel. int.)=1790.2 (100%) [M+].

Example 3

Cyclodehydrogenation to N,N'-bis(2,6-diisopropylphenyl)-1,6,9,22-tetra(2,6-diisoropylphenylphenoxy)pentarylene-3,4:15,16-tetracarboximide A mixture of 0.05 g (0.028 mmol) of the product from example 2, 0.10 g (0.72 mmol) of potassium carbonate, 2.0 ml of ethanolamine and 1.0 ml of diethyl glycol diethyl ether is heated to 120° C. under a nitrogen atmosphere. After 48 h, the reactant has been converted completely.

After cooling, the reaction product is precipitated from water, filtered off, and washed with hot water and then with hexane until the effluent becomes colorless. The residue is subjected to an overnight Soxhlet extraction with hexane. The product is dried at 70° C. under reduced pressure.

30 mg of product are obtained in the form of a black-green solid, which corresponds to a yield of 61%.

Analytical Data:

UV-Vis (CH₂Cl₂): $\lambda_{max}$=871, 780 nm;

MS (Maldi): m/z (rel. int.)=1788.1 (100%) [M+].

The invention claimed is:
1. A pentarylenetetracarboximide of formula (I) or (Ia) or a mixture thereof

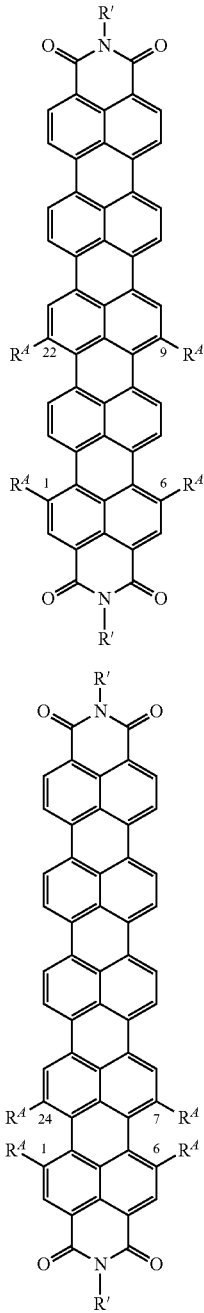

wherein
each $R^A$ is the same or different and is independently the following radical:
H;
aryloxy, arylthio, hetaryloxy, or hetarylthio, to each of which is optionally fused further saturated or unsaturated 5- to 7-membered rings whose carbon skeleton is optionally interrupted by one or more —O—, —S—, —NR$^1$—, —N═CR$^1$—, —CO—, —SO— and/or —SO$_2$— moieties, wherein the aryloxy, arylthio, hetaryloxy, or hetarylthio, optionally fused, in its entirety, is optionally mono- or polysubstituted by the (i), (ii), (iii), (iv) and/or radicals:
(i) $C_1$-$C_{30}$-alkyl whose carbon chain is optionally interrupted by one or more —O—, —S—, —NR$^1$—, —N═CR$^1$—, —C≡C—, CR$^1$═CR$^1$—, —CO—, —SO— and/or —SO$_2$— moieties, optionally mono- or polysubstituted by: $C_1$-$C_{12}$-alkoxy, $C_1$-$C_6$ alkylthio, —C≡CR$^1$, CR$^1$═CR$^1{}_2$, hydroxyl, mercapto, halogen, cyano, nitro, —NR$^2$R$^3$, —NR$^2$COR$^3$, —CONR$^2$R$^3$, —SO$_2$NR$^2$R$^3$, —COOR$^2$, —SO$_3$R$^2$, —PR$^2$R$^3$, —POR$^2$R$^3$, aryl, and/or saturated or unsaturated $C_4$-$C_7$-cycloalkyl whose carbon skeleton is optionally interrupted by one or more —O—, —S—, —NR$^1$—, —N═CR$^1$—, —CR$^1$═CR$^1$—, —CO—, —SO—, and/or —SO$_2$-moieties, wherein the aryl and cycloalkyl radicals are each optionally mono- or polysubstituted by $C_1$-$C_{16}$-alkyl and/or the above radicals specified as substituents for alkyl;
(ii) $C_3$-$C_8$-cycloalkyl whose carbon skeleton is optionally interrupted by one or more —O—, —S—, —NR$^1$—, —N═CR$^1$—, —CR$^1$═CR$^1$—, —CO—, —SO— and/or —SO$_2$—, moieties, optionally fused to one or more further saturated or unsaturated 5- to 7-membered rings whose carbon skeleton is optionally interrupted by one or more —O—, —S—, —NR$^1$—, —N═CR$^1$—, —CR$^1$═CR$^1$—, —CO—, —SO— and/or —SO$_2$— moieties, wherein the cycloalkyl, optionally fused, in its entirety, is optionally mono- or polysubstituted by: $C_1$-$C_{18}$-alkyl, $C_1$-$C_{12}$-alkoxy, $C_1$-$C_6$-alkylthio, —C≡CR$^1$, —CR$^1$═CR$^1{}_2$,hydroxyl, mercapto, halogen, cyano, nitro, —NR$^2$R$^3$, —NR$^2$COR$^3$, —CONR$^2$R$^3$, —SO$_2$NR$^2$R$^3$, —COOR$^2$, —SO$_3$R$^2$, —PR$^2$R$^3$, and/or —POR$^2$R$^3$;
(iii) aryl or hetaryl to which is optionally fused one or more further saturated or unsaturated 5- to 7-membered rings whose carbon skeleton is optionally interrupted by one or more —O—, —S—, —NR$^1$—, —N═CR$^1$—, —CR$^1$═CR$^1$—, —CO—, —SO— and/or —SO$_2$— moieties, where the entire ring system is optionally mono- or polysubstituted by: $C_1$-$C_{16}$-alkyl, $C_1$-$C_{12}$-alkoxy, $C_1$-$C_6$-alkylthio, —C≡CR$^1$, —CR$^1$═CR$^1{}_2$, hydroxyl, mercapto, halogen, cyano, nitro, —NR$^2$R$^3$, —NR$^2$COR$^3$, —CONR$^2$R$^3$, —SO$_2$NR$^2$R$^3$, —COOR$^2$, —SO$_3$R$^2$, —PR$^2$R$^3$, —POR$^2$R$^3$, aryl, and/or hetaryl, each of which is optionally substituted by $C_1$-$C_{18}$-alkyl, $C_1$-$C_{12}$-alkoxy, hydroxyl, mercapto, halogen, cyano, nitro, —NR$^2$R$^3$, —NR$^2$COR$^3$, —CONR$^2$R$^3$, —SO$_2$NR$^2$R$^3$, —COOR$^2$, —SO$_3$R$^2$, —PR$^2$R$^3$, and/or —POR$^2$R$^3$;
(iv) a —U-aryl radical which is optionally mono- or polysubstituted by the by the above radicals specified as substituents for the aryl radicals (iii), wherein U is a —O—, —S—, —NR$^1$—, —CO—, —SO—, or —SO$_2$— moiety;
(v) $C_1$-$C_{12}$-alkoxy, $C_1$-$C_6$-alkylthio, —C≡CR$^1$, —CR$^1$═CR$^1{}_2$, hydroxyl, mercapto, halogen, cyano, nitro, —NR$^2$R$^3$, —NR$^2$COR$^3$, —CONR$^2$R$^3$, —SO$_2$NR$^2$R$^3$, —COOR$^2$, —SO$_3$R$^2$, —PR$^2$R$^3$, and/or —POR$^2$R$^3$;
$R^1$ is hydrogen or $C_1$—$C_{18}$-alkyl, wherein $R^1$ radicals are optionally the same or different when they occur more than once;
$R^2$, $R^3$ are each independently hydrogen;
$C_1$-$C_{18}$-alkyl whose carbon chain is optionally interrupted by one or more —O—, —S—, —CO—, —SO—, and/ or -SO$_2$— moieties and optionally mono- or poly-substituted by $C_1$-$C_{12}$-alkoxy, $C_1$-$C_8$-alkylthio, hydroxyl, mercapto, halogen, cyano, nitro, and/or —COOR$^1$;
aryl or hetaryl, to each of which is optionally fused one or more further saturated or unsaturated 5- to 7-membered rings whose carbon skeleton is optionally interrupted by one or more —O—, —S—, —CO—, and/or —SO$_2$— moieties, wherein the aryl or hetaryl, optionally fused, in its entirety, is optionally mono- or polysubstituted by $C_1$-$C_{12}$-alkyl and/or the above radicals specified as substituents for alkyl;

each R' is independently hydrogen;

$C_1$-$C_{30}$-alkyl whose carbon chain is optionally interrupted by one or more —O—, —S—, —NR$^1$, N=CR$^1$—, —C≡C—, —CR$^1$=CR$^1$—, —CO—, —SO—, and/or —SO$_2$— moieties, or optionally mono- or polysubstituted by the (ii), (iii), (iv) and/or (v) radicals specified as substituents for the $R^4$ radicals;

$C_3$-$C_8$-cycloalkyl to which is optionally fused one or more further saturated or unsaturated 5- to 7-membered rings whose carbon skeleton is optionally interrupted by one or more —O—, —S—, —NR$^1$—, —N=CR$^1$—, —CR$^1$=CR$^1$—, —CO—, —SO—, and/or —SO$_2$— moieties, wherein the cycloalkyl, optionally fused, in its entirety, is optionally substituted by the (i), (ii), (iii), (iv) and/or (v) radicals specified as substituents for the $R^4$ radicals; or aryl or hetaryl, to which is optionally fused one or more further saturated or unsaturated 5 to 7-membered rings whose carbon skeleton is optionally interrupted by one or more —O—, —S—, —NR$^1$—, —N=CR$^1$—, —CR$^1$=CR$^1$—, —CO—, —SO—, and/or —SO$_2$- moieties, wherein aryl or hetaryl, optionally fused, in its entirety, is optionally substituted by the (i), (ii), (iii), (iv), (v) radicals specified as substituents for the $R^4$ radicals, aryl-and/or hetarylazo, each of which is optionally substituted by $C_1$-$C_{10}$-alkyl, $C_1$-$C_6$-alkoxyl and/or cyano;

with the proviso that at least three $R^4$ in formula (I) or (Ia) are different than H.

2. The pentarylenetetracarboximide according to claim 1 or a mixture thereof, wherein all four $R^4$ in formula (I) or (Ia) are different than H.

3. The pentarylenetetracarboximide according to claim 1 or a mixture thereof, wherein $R^4$ in the 22 position in formula (I) or $R^4$ in the 24 position in formula (Ia) is H.

4. The pentarylenetetracarboximide according to claim 1 or a mixture thereof of the formula (I).

5. The process for preparing pentarylenetetracarboximides according to claim 1, comprising (a) coupling at least one terrylene compound of formula (II) or (IIa)

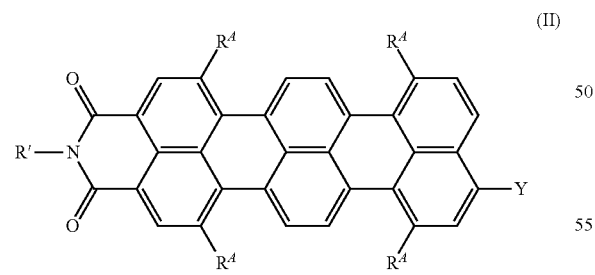

(II)

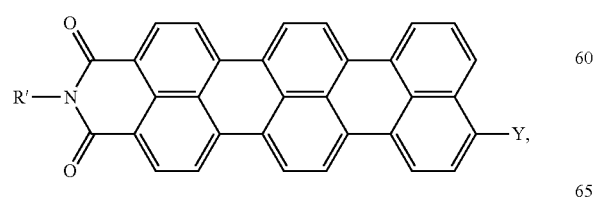

(IIa)

with at least one compound of the formula (III) or (IIIa)

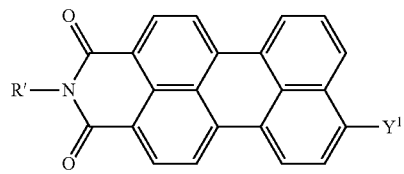

(III)

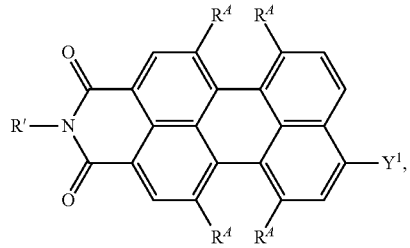

(IIIa)

wherein

Y, $Y^1$ are each halogen or one radical of Y, $Y^1$ is halogen and the other is B(OR")$_2$;

each R" is independently hydrogen, $C_1$-$C_{30}$-alkyl, $C_5$-$C_8$-cycloalkyl, aryl or hetaryl or, joined together to form a 5- to 7-membered ring comprising the two oxygen atoms and the boron atom, is optionally fused to the unsaturated or saturated rings, wherein said 5- to 7-membered ring ring is optionally substituted on the carbon atoms by up to 4 $C_1$-$C_{30}$-alkyl, $C_5$-$C_8$-cycloalkyl, aryl, or hetaryl groups; and each R' and $R^4$ is as defined in claim 1, to give a first reaction product;

(b) cyclodehydrogenating the first reaction product obtained in (a) to give a pentarylene compound of general formula (I) or (Ia) or a mixture thereof.

6. A pentarylenetetracarboximide precursor of the formula (Ib) or (Ic) or a mixture thereof

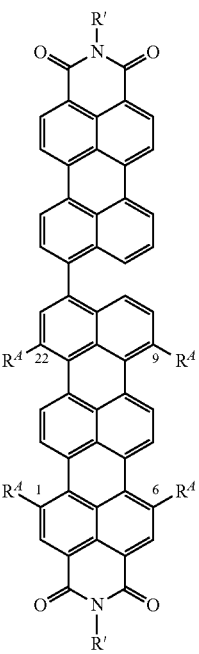

(Ib)

(Ic)

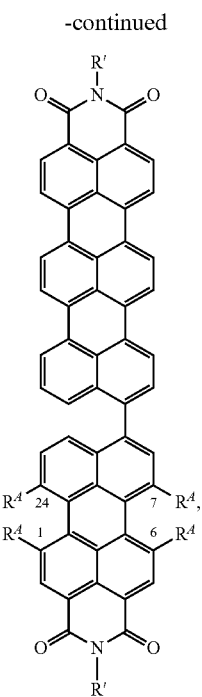

wherein
each $R^A$ is the same or different and is independently the following radical:

H;

aryloxy, arylthio, hetaryloxy, or hetarylthio, to each of which is optionally fused further saturated or unsaturated 5- to 7-membered rings whose carbon skeleton is optionally interrupted by one or more —O—, —S—, —NR$^1$—, —N═CR$^1$—, —CO—, —SO— and/or —SO$_2$— moieties, wherein the aryloxy, arylthio, hetaryloxy, or hetarylthio, optionally fused, in its entirety, is optionally mono- or polysubstituted by the (i), (ii), (iii), (iv) and/or (v) radicals:

(i) $C_1$-$C_{30}$-alkyl whose carbon chain is optionally interrupted by one or more —O—, —S—, —NR$^1$—, —N═CR$^1$—, —C≡C—, CR$^1$═CR$^1$—, —CO—, —SO— and/or —SO$_2$— moieties, optionally mono- or polysubstituted by: $C_1$-$C_{12}$-alkoxy, $C_1$-$C_6$-alkylthio,— C≡CR$^1$, —CR$^1$═CR$^1$$_2$, hydroxyl, mercapto, halogen, cyano, nitro, —NR$^2$R$^3$, —NR$^2$COR$^3$, —CONR$^2$R$^3$, —SO$_2$NR$^2$R$^3$, —COOR$^2$, —SO$_3$R$^2$, —PR$^2$R$^3$, —POR$^2$R$^3$, aryl, and/or saturated or unsaturated $C_4$-$C_7$-cycloalkyl whose carbon skeleton is optionally interrupted by one or more —O—, —S—, —NR$^1$—, —N═CR$^1$—, —CR$^1$═CR$^1$—, —CO—, —SO—, and/or —SO$_2$-moieties, wherein the aryl and cycloalkyl radicals are each optionally mono- or polysubstituted by $C_1$-$C_{16}$-alkyl and/or the above radicals specified as substituents for alkyl;

(ii) $C_3$-$C_8$-cycloalkyl whose carbon skeleton is optionally interrupted by one or more —O—, —S—, —NR$^1$—, —N═CR$^1$—, —CR$^1$═CR$^1$—, —CO—, —SO— and/or —SO$_2$—, moieties, optionally fused to one or more further saturated or unsaturated 5-to 7-membered rings whose carbon skeleton is optionally interrupted by one or more —O—, —S—, —NR$^1$—, —N═CR$^1$—, —CR$^1$═CR$^1$—, —CO—, —SO— and/or —SO$_2$— moieties, wherein the cycloalkyl, optionally fused, in its entirety, is optionally mono- or polysubstituted by: $C_1$-$C_{18}$-alkyl, $C_1$-$C_{12}$-alkoxy, $C_1$-$C_6$-alkylthio, —C≡CR$^1$, —CR═CR$^1$$_2$, hydroxyl, mercapto, halogen, cyano, nitro, —NR$^2$R$^3$, —NR$^2$COR$^3$, —CONR$^2$R$^3$, —SO$_2$NR$^2$R$^3$, —COOR$^2$, —SO$_3$R$^2$, —PR$^2$R$^3$, and/or —POR$^2$R$^3$;

(iii) aryl or hetaryl to which is optionally fused one or more further saturated or unsaturated 5- to 7-membered rings whose carbon skeleton is optionally interrupted by one or more —O—, —S—, —NR$^1$—, —N═CR$^1$—, —CR$^1$═CR$^1$—, —CO—, —SO—and/or —SO$_2$— moieties, where the entire ring system is optionally mono- or polysubstituted by: $C_1$-$C_{16}$-alkyl, $C_1$-$C_{12}$-alkoxy, $C_1$-$C_6$-alkylthio, —C≡CR$^1$, —CR$^1$═CR$^1$$_2$, hydroxyl, mercapto, halogen, cyano, nitro, —NR$^2$R$^3$, —NR$^2$COR$^3$, —CONR$^2$R$^3$, —SO$_2$NR$^2$R$^3$, —COOR$^2$, —SO$_3$R$^2$, —PR$^2$R$^3$, —POR$^2$R$^3$, aryl, and/or hetaryl, each of which is optionally substituted by $C_1$-$C_{18}$-alkyl, $C_1$-$C_{12}$-alkoxy, hydroxyl, mercapto, halogen, cyano, nitro, —NR$^2$R$^3$, —NR$^2$COR$^3$, —CONR$^2$R$^3$, —SO$_2$NR$^2$R$^3$, —COOR$^2$, —SO$_3$R$^2$, —PR$^2$R$^3$, and/or —POR$^2$R$^3$;

(iv) a —U-aryl radical which is optionally mono- or polysubstituted by the above radicals specified as substituents for the aryl radicals (iii), wherein U is a —O—, —S—, —NR$^1$—, —CO—, —SO—, or —SO$_2$— moiety;

(v) $C_1$-$C_{12}$-alkoxy, $C_1$-$C_6$-alkylthio, —C≡CR$^1$, —CR$^1$═CR$^1$$_2$, hydroxyl, mercapto, halogen, cyano, nitro, —NR$^2$R$^3$, —NR$^2$COR$^3$, —CONR$^2$R$^3$, —SO$_2$NR$^2$R$^3$, —COOR$^2$, —SO$_3$R$^2$, —PR$^2$R$^3$, and/or —POR$^2$R$^3$;

$R^1$ is hydrogen or $C_1$-$C_{18}$-alkyl, wherein $R^1$ radicals are optionally the same or different when they occur more than once;

$R^2$, $R^3$ are each independently hydrogen;

$C_1$-$C_{18}$-alkyl whose carbon chain is optionally interrupted by one or more —O—, —S—, —CO—, —SO—, and/or —SO$_2$— moieties and optionally mono- or polysubstituted by $C_1$-$C_{12}$-alkoxy, $C_1$-$C_8$-alkylthio, hydroxyl, mercapto, halogen, cyano, nitro, and/or —COOR$^1$;

aryl or hetaryl, to each of which is optionally fused one or more further saturated or unsaturated 5- to 7-membered rings whose carbon skeleton is optionally interrupted by one or more —O—, —S—, —CO—, and/or —SO$_2$— moieties, wherein the aryl or hetaryl, optionally fused, in its entirety, is optionally mono- or polysubstituted by $C_1$-$C_{12}$-alkyl and/or the above radicals specified as substituents for alkyl;

each R' is independently hydrogen;

$C_1$-$C_{30}$-alkyl whose carbon chain is optionally interrupted by one or more —O—, —S—, —NR$^1$, N═CR$^1$—, —C≡C—, —CR$^1$═CR$^1$—, —CO—, —SO—, and/or —SO$_2$— moieties, or optionally mono- or polysubstituted by the (ii), (iii), (iv) and/or (v) radicals specified as substituents for the $R^A$ radicals;

$C_3$-$C_8$-cycloalkyl to which is optionally fused one or more further saturated or unsaturated 5- to 7-membered rings whose carbon skeleton is optionally interrupted by one or more —O—, —S—, —NR$^1$—, —N═CR$^1$—, —CR$^1$═CR$^1$—, —CO—, —SO—, and/or —SO$_2$— moieties, wherein the cycloalkyl, optionally fused, in its entirety, is optionally substituted by the (i), (ii), (iii), (iv) and/or (v) radicals specified as substituents for the $R^A$ radicals; or aryl or hetaryl, to which is optionally fused one or more further saturated or unsaturated 5 to 7-membered rings whose carbon skeleton is optionally interrupted by one or more —O—, —S—, —NR$^1$—, —N═CR$^1$—, —CR$^1$═CR$^1$—, —CO—, —SO—, and/or —SO$_2$-moieties, wherein aryl or hetaryl, optionally fused, in its entirety, is optionally substituted by the (i), (ii), (iii), (iv), (v) radicals specified as substituents for the $R^A$ radicals, aryl-and/or hetarylazo, each of which is optionally substituted by $C_1$-$C_{10}$-alkyl, $C_1$-$C_6$-alkoxy, and/or cyano;

with the proviso that at least three $R^A$ in formula (Ib) or (Ic) are different than H.

7. An organic or inorganic polymer material, an organic pigment composition, an aqueous polymer dispersion, a marking or inscription, a heat management system, an IR laserbeam absorbing material, a semiconductor composition, an electro-or chemiluminescent device, or a photovoltaic comprising the pentarylenetetracarboximide or a mixture thereof according to claim 1.

8. An organic or inorganic polymer material, an organic pigment composition, an aqueous polymer dispersion, a marking or inscription, a heat management system, an IR laserbeam absorbing material, a semiconductor composition, an electro-or chemiluminescent device, or a photovoltaic device, comprising the precursor according to claim 6 or a mixture thereof.

* * * * *